(12) United States Patent
Konya et al.

(10) Patent No.: US 6,331,652 B1
(45) Date of Patent: Dec. 18, 2001

(54) PROCESS FOR PRODUCING LYCOPENE AND INTERMEDIATE THEREOF

(75) Inventors: Naoto Konya, Takatsuki; Shinzo Seko, Toyonaka, both of (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/624,860

(22) Filed: Jul. 24, 2000

(30) Foreign Application Priority Data

Jul. 26, 1999 (JP) .................................. 11-210597

(51) Int. Cl.$^7$ ............................ C07F 9/54; C07C 317/02; C07C 2/00
(52) U.S. Cl. .................. 568/9; 568/11; 568/32; 585/15; 585/600
(58) Field of Search .................... 568/28, 32, 9, 568/11; 585/600, 15

(56) References Cited

U.S. PATENT DOCUMENTS

| | | | |
|---|---|---|---|
| 3,850,991 | * | 11/1974 | Chabardes et al. |
| 4,331,814 | * | 5/1982 | Chabardes et al. ............ 560/255 |
| 4,883,887 | * | 11/1989 | Bernhard et al. ............. 549/341 |
| 5,166,445 | * | 11/1992 | Meyer ............................ 568/2 |
| 5,973,179 | * | 10/1999 | Babler ........................... 558/83 |
| 6,160,181 | * | 12/2000 | Seko et al. ..................... 568/32 |
| 6,187,959 | * | 2/2001 | Wegner et al. ................. 568/9 |

FOREIGN PATENT DOCUMENTS

| | | |
|---|---|---|
| 2554924 | 6/1977 | (DE) . |
| 0983998A1 | 3/2000 | (EP) . |

OTHER PUBLICATIONS

Pure and Applied Chemistry vol. 63 No. 1 by Bernhard and Mayer pp 35–44 1991.*
Muller, R. K. et al, Pure & Appl. Chem. vol. 69, No. 10, pp. 2039–2046, 1997.
Davis, J. B. et al, Proc. Chem. Soc. 1961, pp. 261–263.
Isler, von O. et al, Helv Chim. Acta. vol. 39, pp. 463–473, 1956.
Nurrenbach, A. et al, Liebigs Ann. Chem. pp. 1146–1159, 1977.

* cited by examiner

Primary Examiner—Jean F. Vollano
(74) Attorney, Agent, or Firm—Birch, Stewart, Kolasch & Birch, LLP

(57) ABSTRACT

There are disclosed
a sulfonaldehyde derivative of formula (2):

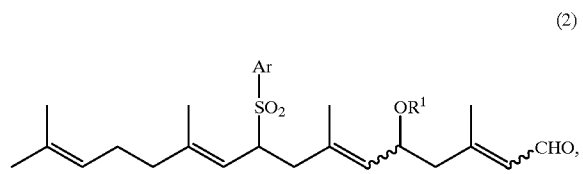

a phosphonium salt of formula (3):

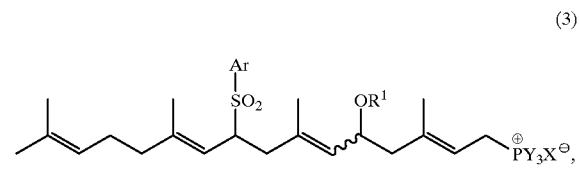

processes for producing the same and a sulfone derivative of formula (4):

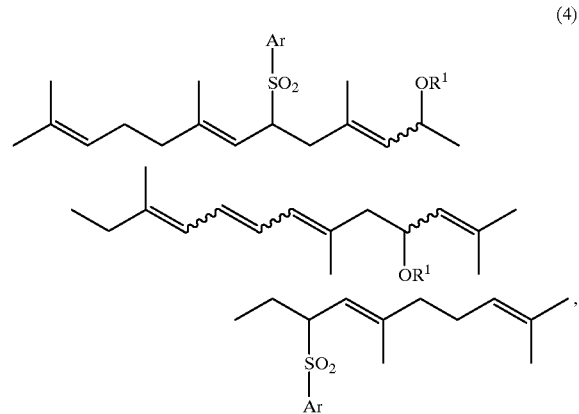

a process for producing the same and a process for producing lycopene therefrom.

20 Claims, No Drawings

PROCESS FOR PRODUCING LYCOPENE AND INTERMEDIATE THEREOF

BACKGROUND OF THE INVENTION

1. Field of the Invention

The present invention relates to a process for the production of lycopene, a carotenoid that is important in the fields of medicines, feed additives and food additives and also to an intermediate of lycopene.

2. Description of Related Art

For the synthesis of lycopene, which is a symmetric C40 compound, there have been known following methods such as a method of coupling two C15 compounds and a C10 compound, a method of coupling two C10 compounds and a C20 compound (e.g., Pure & Appl. Chem., Vol. 69, 2039 (1997) or Helv. Chim. Acta, Vol. 39, 463 (1956)) and a method of coupling two C8 compounds and a C24 compound (e.g., DE 2554924 A1). However, these methods were not always satisfactory in that they required to synthesize two different compounds of different carbon numbers and molecular structures. There have also been known methods of coupling two C20 compounds as reported in Proc. Chem. Soc., 261 (1961) and Liebigs Ann. Chem., 1146 (1977), however, these methods are not always practical from an industrial point of view because they required multistep Wittig reactions and oxidation-reduction reactions to obtain C20 compounds.

SUMMARY OF THE INVENTION

An object of the invention is to provide a method for producing lycopene using a novel intermediate compound.

Further objects of the invention are to provide industrially advantageous two C20 compounds for producing the intermediate compound and methods for producing the two C20 compounds from an inexpensive C10 compound linalool or geraniol in an industrially advantageous manner.

The present invention provides:

1. a process for producing a sulfonaldehyde derivative of formula (2):

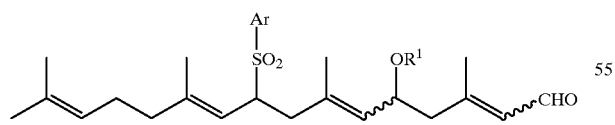

(2)

wherein Ar represents an aryl group which may be substituted, $R^1$ represents a lower alkyl group or a protective group of a hydroxyl group and the wavy line depicted by "⁓" indicates a single bond and stereochemistry relating to a double bond bound therewith is E or Z or a mixture thereof, which comprises oxidizing a sulfone alcohol derivative of formula (1):

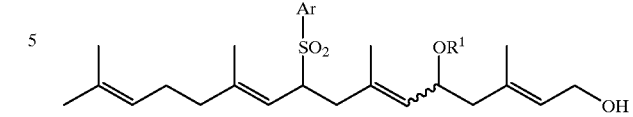

(1)

wherein Ar, $R^1$ and the wavy line respectively have the same meanings as defined above;

2. a sulfonaldehyde derivative of formula (2) as defined above;
3. a process for producing a phosphonium salt of formula (3):

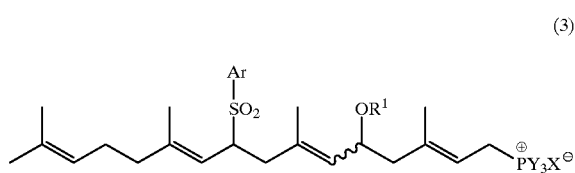

(3)

wherein Ar, $R^1$ and the wavy line respectively have the same meanings as defined above, Y represents a lower alkyl group or an optionally substituted aryl group, and X represents a halogen atom or $HSO_4$, which comprises reacting a sulfone alcohol derivative of formula (1) with a salt of a tertiary phosphine compound of formula: $PY_3$, and a protonic acid, or with a tertiary phosphine compound of formula: $PY_3$, in the presence of a protonic acid, wherein Y represents the same as defined above;

4. a phosphonium salt of formula (3) as defined above;
5. a process for producing a sulfone derivative of formula (4):

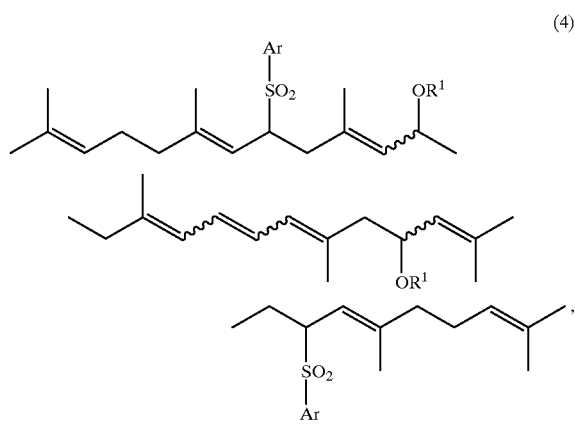

(4)

wherein Ar and $R^1$ are the same or different and independently represent the same as defined above and the wavy line has the same meanings as defined above,
which comprises reacting a phosphonium salt of formula (3) as defined above with a sulfonaldehyde derivative of formula (2) as defined above in the presence of a base or an epoxide;

6. a sulfone derivative of formula (4) as defined above; and
7. a process for producing lycopene of formula (5):

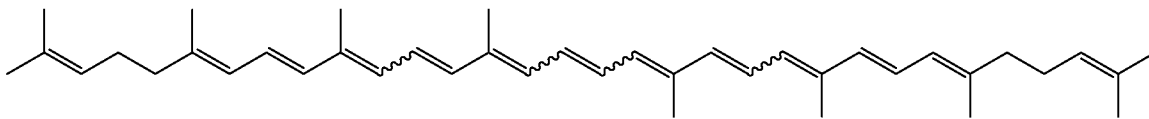

(5)

wherein the wavy line has the same meaning as defined above, which comprises reacting a sulfone derivative of formula (4) as defined above with a basic compound.

DESCRIPTION OF THE PREFERRED EMBODIMENTS

The present invention will be hereinafter explained in detail.

The protective group of a hydroxyl group in the substituent $R^1$ of the sulfone alcohol derivative (1), sulfonaldehyde derivative (2), phosphonium salt (3) and sulfone derivative (4) in the present invention include an acyl group, a silyl group, an alkoxyalkyl group, an aralkyl group, a hydrocarbyloxycarbonyl group and the like.

Examples of the acyl group include a group of formula: Q-C=O, wherein Q is a hydrogen atom, a (C1–C6)alkyl group or a phenyl group which may be substituted with a (C1–C3) alkyl group, a (C1–C3)alkoxy group, a halogen atom or a nitro group.

Specific examples thereof include an acetyl, pivaloyl, benzoyl, p-nitrobenzoyl group, p-methylbenzoyl group, p-methoxybenzoyl group and the like.

Examples of the silyl group include a silyl group substituted with three groups selected from a (C1–C4)alkyl group and a phenyl group. Specific examples thereof include trimethylsilyl, t-butyldimethylsilyl, t-butyldiphenylsilyl group and the like.

Examples of the alkoxyalkyl group include a (C2–C5) alkoxyalkyl group such as tetrahydropyranyl, methoxymethyl, methoxyethoxymethyl, 1-ethoxyethyl and the like.

Examples of the aralkyl group include a methyl group substituted with at least one phenyl group, which phenyl group may be substituted with a (C1–C3)alkyl group(e.g. methyl, ethyl, n-propyl, i-propyl), a (C1–C3)alkoxy group (methoxy, ethoxy, n-propoxy, i-propoxy), a halogen atom, a nitro group and the like. Specific examples thereof include a benzyl group, p-methoxybenzyl group, p-nitrobenzyl group, tributyl group, a benzhydryl group and the like.

Examples of the hydrocarbyloxycarbonyl group include a (C1–C7) alkyl- or aralkyl-oxycarbonyl group such as a benzyloxycarbonyl group, a t-butoxycarbonyl group, a methoxycarbonyl group, ethoxycarbonyl group, n-propoxycarbonyl group or the like.

Examples of the lower alkyl group in the substituent $R^1$ include a (C1–C4) straight or branched chain alkyl group such as a methyl, ethyl, n-propyl, isopropyl, n-butyl, isobutyl or t-butyl group.

Preferred are the lower alkyl group and acyl groups for $R^1$.

Examples of the aryl group which may be substituted represented by "Ar" include a phenyl group and a naphthyl group, both of which may be substituted with at least one group selected from a C1 to C6 alkyl group(e.g. a methyl, ethyl, n-propyl, i-propyl, n-butyl, s-butyl, i-butyl, t-butyl, n-pentyl, t-amyl, or n-hexyl group), a C1 to C6 alkoxy group(e.g. a methoxy, ethoxy, n-propoxy, i-propoxy, n-butoxy, s-butoxy, i-butoxy, t-butoxy, n-pentyloxy, t-amyloxy, or n-hexyloxy group), a halogen atom and a nitro group.

Specific examples thereof include a phenyl, naphthyl, o-tolyl, m-tolyl, p-tolyl, o-methoxyphenyl, m-methoxyphenyl, p-methoxyphenyl, o-chlorophenyl, m-chlorophenyl, p-chlorophenyl, o-bromophenyl, m-bromophenyl, p-bromophenyl, o-iodophenyl, m-iodophenyl, p-iodophenyl, o-fluorophenyl, m-fluorophenyl, p-fluorophenyl, o-nitrophenyl, m-nitrophenyl and p-nitrophenyl group.

The substituent X of the phosphonium salt (3) represents a halogen atom (e.g. a chlorine atom, bromine atom and iodine atom) or $HSO_4$.

The sulfonaldehyde derivative (2) can be obtained by a process which comprises oxidizing, the sulfone alcohol derivative (1).

The oxidizing of the sulfone alcohol derivative (1) is usually conducted by one of the following methods and the like.

The oxidizing of the sulfone alcohol derivative (1) can be conducted by (a) subjecting the sulfone alcohol derivative (1) to contact with a metal oxidant.

Alternatively, the oxidizing may be conducted by (b) subjecting the sulfone alcohol derivative (1) to contact with a sulfoxide compound, a sulfoxide-activating compound and optionally a base, or (c) subjecting the sulfone alcohol derivative (1) to contact with a sulfide compound, a halogenating agent and a base, or (d) subjecting the sulfone alcohol derivative (1) to contact with an aldehyde in the presence of a catalyst selected from an aluminum alkoxide or aryloxide, and a boron compound, or (e) subjecting the sulfone alcohol derivative (1) to contact with an oxygen in the presence of a catalyst.

A description will be made to the oxidizing reaction (a).

Examples of the metal oxidant include a salt or oxide of chromium or manganese, an oxide of nickel or selenium, or a salt of silver. Specific examples thereof include pyridinium chlorochromate, pyridinium dichromate, manganese dioxide, nickel peroxide, selenium dioxide and silver carbonate. The amount of the metal oxidant to be used is usually about 1 to 20 moles, preferably 1 to 10 moles per mol of the sulfone alcohol derivative (1).

The reaction is usually conducted in a solvent. Examples of the solvent include a hydrocarbon solvent such as n-hexane, cyclohexane, n-pentane, n-heptane, toluene or xylene, a halogenated hydrocarbon solvent such as chloroform, dichloromethane, 1,2-dichloroethane, monochlorobenzene, o-dichlorobenzene or α,α,α-trifluorotoluene, an aprotic polar solvent such as N,N-dimethylformamide, dimethylsulfoxide, acetonitrile, N,N-dimethylacetamide or hexamethylphosphoric triamide or an ether solvent such as 1,4-dioxane, tetrahydrofuran or anisole. The reaction temperature is usually in a range between about 0° C. and 50° C.

After completion of the reaction, the reaction mixture is usually subjected to post-treatments which include filtration to remove the metal oxidant where an organic solvent as listed above or water may be optionally used, phase separation, washing and/or evaporation to give the desired product, which may be further purified by column chromatography or recrystallization, if necessary.

Next, a description will be made to the oxidizing reactions (b) and (c) described above, which may be referred to as "Swern oxidation" or "Corey-Kim oxidation" respectively.

Examples of the sulfoxide compound include a di(C1–C3)alkyl sulfoxide such as dimethylsulfoxide and the like. Examples of the sulfoxide-activating compound include oxalyl chloride, acetic anhydride, thionyl chloride, phosene or the like. The sulfoxide compound and the sulfoxide-activating compound are usually used in an equimolar amount each other. Specific examples of the combination thereof include dimethylsulfoxide and oxalyl chloride, dimethylsulfoxide and any one of the above-described sulfoxide-activating compound other than oxalyl chloride and the like.

Examples of the sulfide compound include a methyl (C1–C3)alkyl sulfide or methylphenylsulfide such as dimethylsulfide and the like. Examples of the halogenating agent to be used with the sulfide compound include N-chlorosuccinimide and the like. The sulfide compound and the halogenating agent are usually used in an equimolar amount each other. Specific examples of the combination thereof include dimethylsulfide and N-chlorosuccinimide, and the like.

The amount of the sulfoxide compound and sulfoxide-activating compound, or the sulfide compound and halogenating agent to be used is usually about 1 to 5 moles, preferably about 1 to 3 moles per mol of the sulfone alcohol derivative (1).

Examples of the base include a (C6–C12)tertiary amine such as triethylamine, tripropylamine or tributylamine. The amount of the base is usually about 1 to 5 moles, preferably 1 to 3 moles per mol of the sulfoxide compound or sulfide compound.

The reaction is usually conducted in a solvent, examples of which include those described for the oxidizing reaction (a) above and an ester solvent such as ethyl acetate or butyl acetate. The reaction temperature is usually in a range of about −80 to 0° C.

Next a description will be made to the reaction (d), which may be referred to as a hydrogen transfer type oxidation reaction (for example, Oppenauer oxidation).

Examples of the aluminum alkoxide or aryloxide to be used in this reaction include a (C3–C7) secondary or tertiary alkoxide or aryloxide of aluminum.

Specific examples thereof include aluminum isopropoxide, aluminum t-butoxide, aluminum s-butoxide and aluminum phenoxide. Examples of the boron compounds include tris(pentafluorophenyl) boron and bis(pentafluorophenyl)boric acid.

Examples of the aldehyde, as a hydrogen acceptor, include a tertiary alkyl or aromatic aldehyde having C5–C7 carbon atoms such as trimethylacetaldehyde, 2,2-dimethylbutanal or benzaldehyde.

The amount of the aluminum alkoxide or aryloxide, or boron compounds may be catalytic and is usually about 0.001 to 0.3 mol, preferably about 0.01 to 0.1 mol per mol of the sulfone alcohol derivative (1).

The amount of the aldehyde is usually about 1 to 10 moles, preferably about 1 to 5 moles per mol of the sulfone alcohol derivative (1).

The reaction is usually conducted in a solvent, examples of which include those described for the oxidizing reaction (a) above. The reaction temperature is usually in a range of about 10 to 60° C.

Next a description will be made to the oxidation reaction (e).

Examples of the catalyst for the oxidation reaction using oxygen include platinum, a catalyst comprising 2,2,6,6-tetramethylpiperidine-1-oxyl (TEMPO) and copper chloride, a catalyst comprising tris(triphenylphosphine) ruthenium and hydroquinone chloride, and a catalyst comprising tetrapropylammonium perruthenate and molecular sieves 4A.

The amount of the catalyst to be used is usually about 0.001 to 0.3 mol, preferably about 0.01 to 0.1 mol per mol of the sulfone alcohol derivative (1). The reaction is usually conducted in a solvent, examples of which include those described for the oxidizing reaction (a) above.

Oxygen may be used either alone or as a mixture with other gases such as air, and it may be either of atmospheric pressure or pressured and may be introduced into the reaction solution. The reaction temperature is usually in a range of about 10° C. to 60° C.

After completion of the above-described reactions of (b) to (e), the reaction mixture is usually subjected to post-treatments which include optionally filtration, washing, phase separation and/or evaporation as described above for the reaction (a) to give the desired products, which may be further purified by column chromatography or recrystallization, if necessary.

Specific examples of the sulfonaldehyde derivative of formula (2) include a sulfonaldehyde derivative of formula (2), wherein Ar is a p-tolyl group and $R^1$ is a methyl group, sulfonaldehyde derivatives of formula (2), wherein Ar is a p-tolyl group and $R^1$ represents any one of the specific protective groups of a hydroxyl group as described above or any one of specific C2–C4 alkyl groups as described above. Further specific examples thereof include sulfonaldehyde derivatives of formula (2), wherein p-tolyl group for $R^1$ is replaced by other specific groups as described above for "Ar" in the above-described specific sulfonaldehyde derivatives.

The phosphonium salt (3) can be obtained by a process which comprises reacting the sulfone alcohol derivative (1) with a salt of a tertiary phosphine compound and a protonic acid, or with a tertiary phosphine compound in the presence of a protonic acid, wherein said tertiary phosphine compound is represented by a formula: $PY_3$, wherein Y has the same meaning as defined above.

Examples of the tertiary phosphine compound include a triphenylphosphine compound of which phenyl group may be substituted with a C1–C3 alkyl or a C1–C3 alkoxy group, and a tri(C1–C6)alkylphosphine.

Specific examples of the triphenylphosphine compound include triphenylphosphine, tri-(o-tolyl)phosphine and the like.

Specific examples of said trialkylphosphine include triethylphosphine, tripropylphosphine, tributylphosphine, triphenylphosphine, triethylphosphine and the like.

Examples of the protonic acid include hydrogen chloride, hydrogen bromide, hydrogen iodide and sulfuric acid Examples of the salt of the tertiary phosphine compound and a protonic acid used in the above reaction include triphenylphosphine hydrochloride, triphenylphosphine hydrobromide or triphenylphosphine hydroiodide.

Examples of the protonic acid allowed to coexist with the tertiary phosphine compound include hydrogen chloride, hydrogen bromide, hydrogen iodide and sulfuric acid.

The amount of the tertiary phosphine compound or its salt with a protonic acid is usually about 0.7 to 2 moles per mol of the sulfone alcohol derivative (1). The amount of the protonic acid allowed to coexist with the tertiary phosphine compound is usually about 0.9 to 1.2 moles per mol of the sulfone alcohol derivative (1).

The reaction is usually conducted in an organic solvent, examples of which include those described for oxidizing reaction (a) above and an alcohol solvent such as methanol or ethanol.

The reaction temperature is usually in a range of 10° C. to 50° C.

The resulting phosphonium salt (3) may be isolated after the reaction, alternatively it may be used as it is in the subsequent reaction without being isolated.

Specific examples of the phosphonium salt (3) include a phosphonium salt (3), wherein "Ar" and $R^1$ have the same meaning as defined for specific examples of the sulfonaldehyde derivative of formula (2) and Y is a phenyl group and X is chlorine, and further examples of compounds of formula (3), wherein Y represents any one of the groups as specified for Y above in place of the phenyl group above. In addition to these phosphonium salt (3), further examples thereof include phosphonium salts of formula (3), wherein X represents bromine or iodine in place of chlorine in the specified compounds above and the like.

The sulfone derivative (4) of the present invention can be obtained by a process which comprises reacting the aforementioned phosphonium salt (3) with the sulfonaldehyde derivative (2) in the presence of a base or an epoxide.

There is no particular limitation as to the base used in the above reaction as long as it does not adversely affect the reaction. Examples of the base include an alkali metal alkoxide such as potassium methoxide, potassium ethoxide, potassium n-butoxide, potassium t-butoxide, sodium methoxide, sodium ethoxide, sodium n-butoxide, or sodium t-butoxide and an alkali metal hydroxide such as potassium hydroxide or sodium hydroxide. An epoxide such as an ethylene oxide or 1,2-butene oxide may be used instead of the base.

The amount of the base or epoxide is usually 1 to 5 moles per mol of the phosphonium salt (3).

The reaction is usually conducted in an organic solvent, examples of which include those described for the oxidizing reaction (a) above. The reaction may also be conducted in a two phase system of an organic solvent immiscible with water such as the hydrocarbon solvent, the halogenated hydrocarbon solvent or the like as referred to in reaction (a) above and water.

The reaction temperature is usually in a range of about −10° C. to 150° C., preferably 0° C. to 100° C.

After completion of the reaction, the reaction mixture is usually subjected to post-treatments which include optionally filtration, washing, phase separation and/or evaporation to give the desired product, which may be further purified by column chromatography or recrystallization, if necessary.

Specific examples of the sulfone derivative (4) include a sulfone derivative of formula (4), wherein "Ar" and $R^1$ have the same meanings as specified for the sulfonaldehyde compound of formula (2) above and the like.

The resulting sulfone derivative (4) can be derivatized to lycopene by a process which comprises reacting the sulfone derivative (4) with a basic compound.

Example of the basic compound to be used in the this reaction include an alkali metal hydroxide, an alkali metal hydride and an alkali metal alkoxide. Specific examples thereof include sodium hydroxide, potassium hydroxide, sodium hydride, potassium hydride, sodium methoxide, potassium methoxide, sodium ethoxide, potassium ethoxide, sodium t-butoxide, potassium t-butoxide and the like. The amount of the basic compound is usually about 2 to 30 moles, preferably 4 to 25 moles per mol of the sulfone derivative (4).

The reaction is usually conducted in an organic solvent, examples of which include those described above for the oxidizing reaction (a) above.

The reaction temperature is usually in a range of −78° C. to the boiling point of the solvent to be used.

After completion of the reaction, the reaction mixture is usually subjected to post-treatments which include optionally filtration, washing, phase separation and/or evaporation as described above to give lycopene, which may be further purified by column chromatography or recrystallization, if necessary.

Since lycopene is liable to be oxidized, said post-treatments are preferably carried out in an inert atmosphere, for example, in a atmosphere of nitrogen or argon, and an antioxidant such as BHT(di-t-butylhydroxytoluene) may be added to the reaction mixture or a solution thereof.

The sulfone alcohol derivative (1), which may be a mixture of geometrical isomers of E and Z, a racemate or an optically active isomer can be used in the present process.

The sulfone alcohol derivative (1) above can be readily synthesized from linalool or geraniol, which is available at relatively low cost, according to the rout as shown by the Scheme 1 described below, wherein R represents a protective. A method for the synthesis of the sulfones (6) is described in J. Org. Chem. Vol. 39, 2135 (1974). The sulfones (6) are coupled with an allyl bromide (7) to obtain a sulfone compound (8) and the protected hydroxyl group of the resulting sulfone compound (8) is subjected to selective deprotection of a primary alcoholic OH group or deprotection and selective protection or alkylation of a secondary alcoholic OH group to obtain the sulfone alcohol derivative (1) (e.g. EP0983998).

Scheme 1

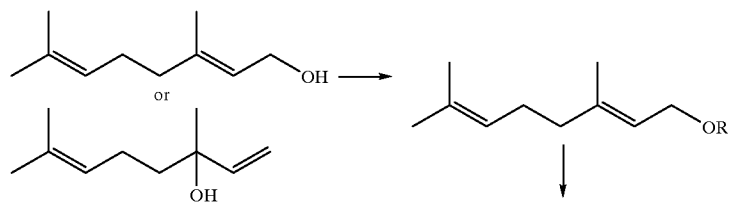

-continued

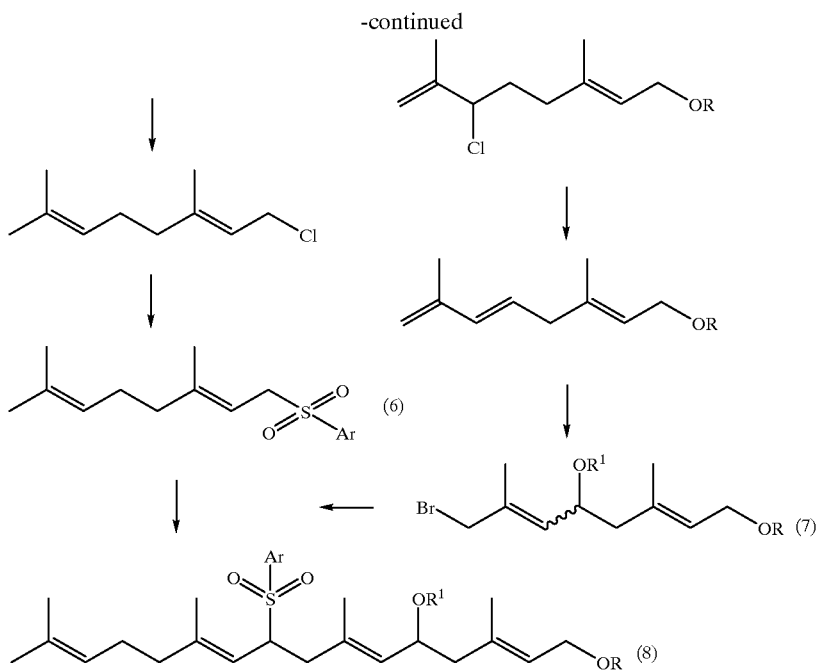

According to the process of the present invention, lycopene which is an important carotenoid in the fields of medicines, feed additives and food additives can be produced fiom readily available linalool or geraniol in an industrially advantageous manner.

EXAMPLES

The present invention will be explained in more detail by way of examples, which are not intended to be limiting of the present invention.

Example 1

712 mg (1.5 mmol) of methoxy alcohol (I) was dissolved in 10 ml of methylene chloride, to which was added 0.65 g of manganese dioxide and the mixture was stirred at an ambient temperature for 17 hours. 0.65 g of manganese dioxide was further added to the mixture, which was then stirred at an ambient temperature for 10 hours and thereafter the reaction solution was diluted with an ether. The diluted solution was dried using anhydrous magnesium sulfate and subjected to filtration. Then the solvent in the filtrate was evaporated to obtain a crude product. The resulting crude product was purified using silica gel column chromatography to give methoxyaldehyde (II) as a pale yellow oil in a yield of 73%.

$^1$H-NMR δ (CDCl$_3$); 1.15–1.22(3H, m), 1.59(3H, s), 1.63(3H, br), 1.60–1.70(2H, m), 1.93(3H, br), 2.10–2.20 (3H, m), 2.43–2.45(3H, m), 2.20–2.40(3H, m), 2.50–3.00 (3H, m), 3.11–3.23(3H, m), 3.75–4.20(2H, m), 4.80–5.30 (3H, m), 5.80–5.95(1H, m), 7.20–7.35(2H, m), 7.60–7.75 (2H, m), 9.84–10.02(1H, m).

Example 2

855 mg (1.8 mmol) of methoxy alcohol (I) was dissolved in 15 ml of methanol, to which was added 700.6 mg (1.98 mmol) of triphenylphosphine hydrobromide and the mixture was then stirred at an ambient temperature for 24 hours. The reaction solution was concentrated to obtain 1.45 g of a crude product of a phosphonium salt (III). The resulting crude product was used as it was in the subsequent reaction.

$^1$H-NMR δ (CDCl3); 1.00–1.30(3H, m), 1.30–1.80(11H, m), 1.80–2.10(3H, m), 2.10–2.60(3H, m), 2.60–3.40(6H, m), 2.45(3H, s), 3.70–4.10(2H, m), 4.30–5.60(5H, m), 5.60–6.40(1H, m), 7.20–8.00(19H, m).

Example 3

94.5 mg (0.2 mmol) of methoxyaldehvde (II) was dissolved in 0.5 ml of methylene chloride, to which was added 0.4 ml of an aqueous solution of 2M sodium hydroxide. To the mixture was added dropwise 0.5 ml of a methylene chloride solution containing 209 mg (0.26 mmol) of the crude product of the phosphonium salt (III) over about 20 minutes and the mixture was stirred at an ambient temperature for 24 hours. Water was added to the reaction solution, which was then subjected to extraction using chloroform. The extract was dried over anhydrous magnesium sulfate, followed by evaporation to obtain a crude product. The resulting crude product was purified by silica gel chromatography to obtain a methoxysulfone (IV) as a yellow oil in a yield of 46%.

$^1$H-NMR δ (CDCl$_3$); 1.10–1.35(6H, m), 1.59(6H, br), 1.67(6H, br), 1.74(6H, br), 1.93(6H, br), 1.40–2.20(12H, m), 2.20–2.50(2H, m), 2.44(6H, s), 2.70–3.05(2H, m), 3.05–3.30(6H, m), 3.70–4.10(4H, m), 4.80–5.30(6H, m), 5.80–6.00(1H, m), 6.00–6.15(1H, m), 6.15–6.50(2H, m), 7.15–7.40(4H, m), 7.50–7.80(4H, m).

Example 4

157.7 mg (0.17 mmol) of the methoxysulfone (IV) was dissolved in 3 ml of tetrahydrofuran, to which was added 182 mg (2.6 mmol) of potassium methoxide. The mixture was stirred at an ambient temperature for 2 hours and thereafter heated under reflux for 7 hours. The temperature of the reaction mixture was then lowered to an ambient temperature. A small amount of methanol was added to the reaction mixture, which was then purified by silica gel chromatography to obtain lycopene (V) in a yield of 85%.

Each structural formula of the compounds (I) to (V) of the Examples is shown in the following.

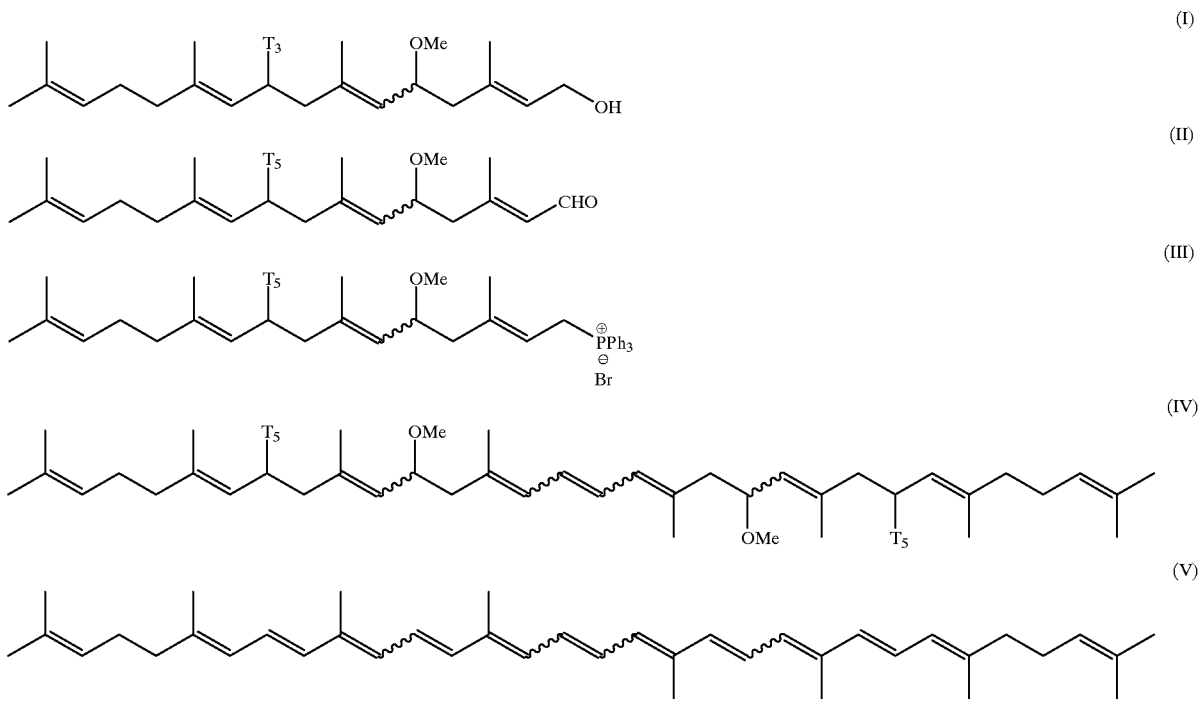

Reference Example 1

40 g (0.204 mol) of geranyl acetate was dissolved in 100 ml of n-hexane, to which was gradually added 17.1 g (0.071 mol) of trichlloroisocyanuric acid and the mixture was kept at −10° C. to 0° C. for 6 hours. After the reaction, excess trichloroisocyanuric acid and by-product isocyanuric acid were removed by filtration. The filtrate was washed with an aqueous sodium bicarbonate solution and water and dried over anhydrous magnesium sulfate, followed by evaporation to obtain a crude product. The resulting crude product was purified by silica gel column chromatography to obtain allyl chloride (a) as a pale yellow oil in a yield of 86%.

$^1$H-NIMR δ (CDCI$_3$); 1.71(3H, s), 1.81(3H, s), 1.90–2.22 (4H, m), 2.05(3H, s), 4.34(1H, t, J=7 Hz), 4.59(2H, d, J=7 Hz), 4.90(1H, s), 5.01(1H, s), 5.37(1H, t, J=7Hz).

Reference Example 2

A dried four necked flask was charged with 6.8 g (0.17 mol) of a fine powdered sodium hydroxide, 2.2 g (8.5 mmol) of triphenylphosphine, 1.4 g (5.1 mmol) of tetra n-butylammonium chloride, 0.62 g (1.7 mmol) of an allylpalladium chloride dimer and 100 ml of THF under a nitrogen atmosphere. 150 ml of a THF solution containing 40 g (0.17 ml) of the above allyl chloride (a) was added dropwise to the mixture at an ambient temperature over one hour with stirring. The resulting mixture was stirred at an ambient temperature for three days, quenched with water and subjected to extraction with ether. The separated organic layer was washed with a saturated brine and dried over anhydrous magnesium sulfate, followed by evaporation to obtain a crude product. The resulting crude product was purified by silica gel chromatography to obtain a triene (b) in a yield of 65%.

$^1$H-NNIR δ (CDCI$_3$); 1.70(3H, s), 1.85(3H, 3), 2.08(3H, s), 2.81(2H, d, J=7Hz), 4.58(2H, d, J=7 Hz), 4.90(2H, s), 5.37(1H, t, J=7 Hz), 5.61(1H, td, J=7, 16 Hz), 6.16(1H, d, =16 Hz).

Reference Example 3

To 20.1 g (0.1 mol) of triene (b) and 100 ml of acetic acid charged in a flask was added 18.3 g (0.1 mol) of N-bromosuccinimide. The reaction mass became clear at an ambient temperature in 10 to 15 minutes. The mixture was stirred for 2 hours, quenched with water and subjected to extraction with toluene. The resulting organic layer was dried over anhydrous magnesium sulfate followed by evaporation to obtain 1,4-bromoacetate (c) (a mixture of an E and a Z isomer) and 1,2-bromoacetate (d) (a mixture of an E and a Z isomer) as an about 1:1 mixture in a yield of 95%. The resulting mixture was separated and purified by silica gel chromatography to obtain the compounds (c) and (d) respectively as a pale yellow oil.

1,4-bromoacetate (c);

$^1$H-NMR δ (CDCI$_3$) 1.77(3H, s), 1.82(3H, s), 1.98(3H, s), 2.02(3H, s), 2.19(2H, m), 3.89(2H, s), 4.55(2H, d, J=7 Hz), 5.37(1H, t, J=7 Hz), 5.48–5.62(2H, m).

1,2-bromoacetate (d)

$^1$H-NMR δ (CDCI$_3$); 1.65(3H, s), 1.68(3H, s), 2.05(3H, s), 2.06(3H, s), 2.78(2H, d, J=6 Hz), 3.67(1H, d, J=11 Hz), 3.82(1H, d, J=11Hz), 4.57(2H, d, J=7 Hz), 5.35(1H, t, J=7 Hz), 5.61–5.77(2H, m).

Reference Example 4

To 2.93 g (10 mmol) of geranyl p-tolylsulfone and 1.55 g (13.8 mmol) of potassium t-butoxide charged in a flask and cooled to −60° C. was added 15 ml of N,N-dimethylfotmamide (DMF) and the mixture was stirred for 30 minutes at the same temperature. 10 ml of a DMF solution containing 3.37 g (10.1 mmol) of 1,4-bromoacetate (c) was added dropwise to the stirred mixture at the same temperature. After the resulting mixture was stirred for 24 hours, it was quenched with an aqueous solution of saturated ammonium chloride and subjected to extraction with ethyl acetate. The resulting organic layer was washed with water and a saturated brine and dried over anhydrous magnesium sulfate, followed by evaporation to obtain a crude product. The resulting crude product was purified by silica gel chromatography to obtain a diacetate (f) as a pale yellow oil in a yield of 70%.

$^1$H-NMR δ (CDCl$_3$); 1.60(3H, s), 1.67(3H, s), 1.70(3H, s), 1.57–1.76(2H, m), 1.93(3H, s), 1.90–2.36(5H, m), 2.00(3H, s), 2.04(3H, s), 2.10(3H, s), 2.44(3H, s), 2.82–2.95(1H, m), 3.79–3.86(1H, m), 4.53(2H, d, J=7 Hz), 4.81–5.15(3H, m), 5.33(1H, m), 5.57(1H, m), 7.29(2H, d, J=8 Hz), 7.67(2H, d, J=8 Hz).

Reference Example 5

2.55 g (4.68 mmol) of the diacetate (f) was dissolved in 10 ml of methanol, to which was added 1.12 g (5.62 mmol) of an aqueous 20% sodium hydroxide solution and the mixture was stirred at an ambient temperature for 2 hours. After the reaction, the mixture was quenched with an aqueous saturated ammonium chloride solution and subjected to extraction with an ether. The resulting organic layer was washed with a saturated brine and dried over anhydrous magnesium sulfate, followed by evaporation to obtain a crude product. The resulting crude product was purified by silica gel column chromatography to obtain a diol (g) as a pale yellow oil in a yield of 95%.

$^1$H NMR δ (CDCl$_3$); 1.55–1.71(4H, m), 1.56(3H, s), 1.62(3H, s), 1.68(6H, s), 1.80–1.94(2H, m), 1.93(3H, s), 2.25–2.41(1H, m), 2.44(3H, s), 2.82–2.95(1H, m), 3.42(1H, br, s), 3.89(1H, t, J=7 Hz), 4.04–4.03(2H, m), 4.38–4.47(1H, m), 4.69(1H, s), 4.90(1H, d, J=7 Hz), 4.98(1H, br), 5.15–5.27(1H, m), 5.45–5.5(1H, t, J=7 Hz), 7.29(2H, d, J=8 Hz), 7.67(2H, d, J=8 Hz).

Reference Example 6

2.50 g (5.43 mmol) of the diol (g) was dissolved in 28 ml of methanol, to which was added 55 mg (0.54 mmol) of 96% concentrated sulfuric acid and the mixture was stirred for 24 hours. After the reaction, the mixture was quenched with an aqueous saturated sodium bicarbonate solution and subjected to extraction with ether. The resulting organic layer was washed with a saturated brine and dried over anhydrous magnesium sulfate, followed by evaporation to obtain a crude product. The resulting crude product was purified by silica gel column chromatography to obtain a methoxy alcohol (I) as a pale yellow oil in a yield of 77%.

$^1$H-NMR δ (CDCl$_3$); 1.18–1.23(3H, m), 1.59(3H, s), 1.67(6H, br), 1.57–1.68(2H, m), 1.93(3H, br), 1.80–2.40(3H, m), 2.41(3H, s), 2.45–3.00(3H, m), 3.11–3.23(3H, m), 3.75–4.20(4H, m), 4.80–5.18(3H, m), 5.30–5.60(1H, m), 7.20–7.35(2H, m), 7.60–7.75(2H, m).

Chemical formulae of the compounds of the Reference Examples are shown in the following.

(a)

(b)

(c)

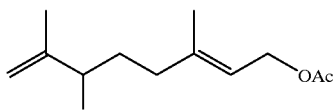

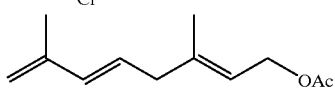

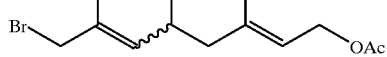

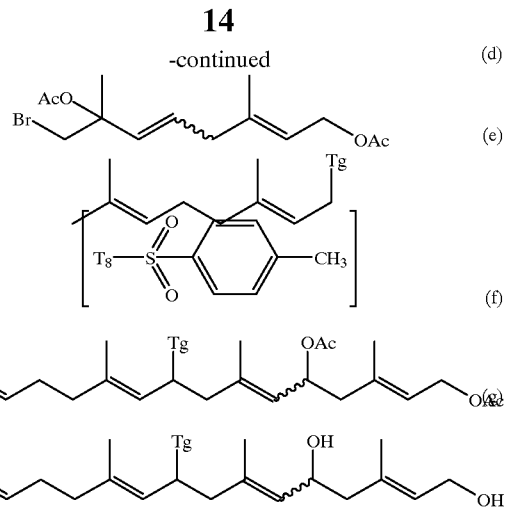

(d)

(e)

(f)

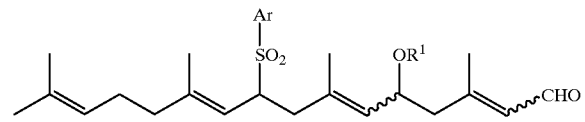

(g)

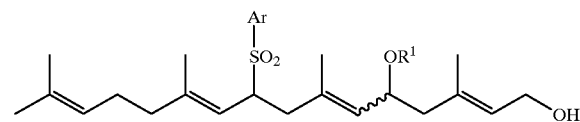

(I)

What is claimed is:

1. A process for producing a sulfonaldehyde derivative of formula (2):

(2)

[Structure of formula (2)]

wherein Ar represents an aryl group which may be substituted,

R$^1$ represents a lower alkyl group or a protective group of a hydroxyl group and the wavy line depicted by "∿" indicates a single bond and stereochemistry relating to a double bond bound therewith is E or Z or a mixture thereof, which comprises oxidizing a sulfone alcohol derivative of formula (1):

(1)

[Structure of formula (1)]

wherein Ar, R$^1$ and the wavy line respectively have the same meanings as defined above.

2. A process according to claim 1, wherein R$^1$ represents an acyl group, a silyl group, an alkoxyalkyl group, an aralkyl group, a hydrocarbyloxycarbonyl group or a lower alkyl group.

3. A process according to claim 1, wherein R$^1$ represents a group of formula: Q—C=O, wherein Q is a hydrogen atom, a (C1–C6) alkyl group or a phenyl group which may be substituted with a (C1–C3) alkyl group, C1–C3 alkoxy group, a halogen atom or a nitro group, a silyl group substituted with three groups selected from a (C1–C4)alkyl group and a phenyl group, a (C2–C5)alkoxyalkyl group, a methyl group substituted with at least one phenyl group, which phenyl group may be substituted with a group selected from a (C1–C3)alkyl group, a (C1–C3)alkoxy group, a halogen atom and a nitro group, a (C1–C7) alkyl- or aralkyl-oxycarbonyl group, a (C1–C4) straight or branched chain alkyl group, and Ar represents a phenyl group and a naphthyl group, both of which may be substituted with at least one group selected from a (C1–C6) alkyl group, a (C1–C6) alkoxy group, a halogen atom or a nitro group.

4. A process according to claim 1, wherein oxidizing of said sulfone alcohol derivative of formula (1) is conducted by subjecting the sulfone alcohol derivative of formula (1) to contact with (a) a metal oxidant, or (b) a sulfoxide compound, a sulfoxide-activating compound and optionally a base, or (c) a sulfide compound, a halogenating agent and a base, or (d) an aldehyde in the presence of a catalyst selected from aluminum alkoxide or aryloxide, and a boron compound, or (e) oxygen in the presence of a catalyst.

5. A process according to claim 1, wherein oxidizing of said sulfone alcohol derivative of formula (1) is conducted by subjecting the sulfone alcohol derivative of formula (1) to contact with a metal oxidant.

6. A sulfonaldehyde derivative of formula (2) as defined in claim 1 or 2 or 3.

7. A process for producing a phosphonium salt of formula (3):

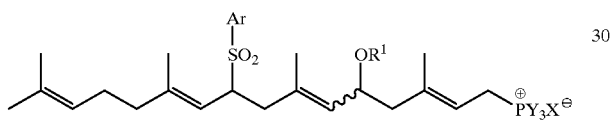

(3)

wherein Ar represents an aiyl group which may be substituted, $R_1$ represents a lower alkyl group or a protective group of a hydroxyl group, the wavy line depicted by "〜" indicates a single bond and stereochemistry relating to a double bond bound therewith is E or Z or a mixture thereof, X represents a halogen atom or $HSO_4$, and Y represents a lower alkyl group or an optionally substituted aryl group, which comprises reacting a sulfone alcohol derivative of formula (1):

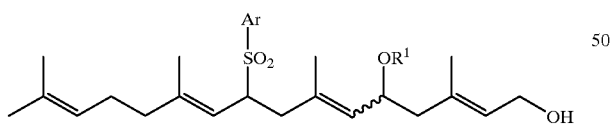

(1)

wherein Ar, $R^1$ and the wavy line respectively have the same meanings as defined above, with a salt of a tertiary phosphine compound and a protonic acid, or with a tertiary phosphine compound in the presence of a protonic acid, wherein said tertiary phosphine compound is represented by a formula: $PY_3$, wherein Y has the same meaning as defined above.

8. A phosphonium salt of formula (3) as defined in claim 7.

9. A phosponium salt according to claim 8, wherein $R^1$ represents an acyl group, a silyl group, an alkoxyalkyl group, an aralkyl group, a hydrocarbyloxycarbonyl group or a lower alkyl group.

10. A phosponium salt according to claim 9, wherein $R^1$ represents a group of formula Q—C=O, wherein Q is a hydrogen atom, a C1–C6 alkyl group or a phenyl group which may be substituted with a C1–C3 alkyl group, C1–C3 alkoxy group, a halogen atom or a nitro group, a silyl group substituted with three groups selected from a (C1–C4)alkyl group and a phenyl group, a (C2–C5)alkoxyalkyl group, a methyl group substituted with at lest one phenyl group, which phenyl group may be substituted with a group selected from a (C1–C3)alkyl group, a (C1–C3)alkoxy group, a halogen atom and a nitro group, a (C1–C7) alkyl- or aralkyl-oxycarbonyl group, a (C1–C4) straight or branched chain alkyl group, Ar represents a phenyl group or a naphthyl group, both of which may be substituted with at least one group selected from a (C1–C6) alkyl group, a (C1–C6) alkoxy group, a halogen atom and a nitro group, and Y represents a C1–C6 alkyl group or a phenyl group which may be substituted with a C1–C3 alkyl group or a C1–C3alkoxy group.

11. A process for producing a sulfone derivative of formula (4):

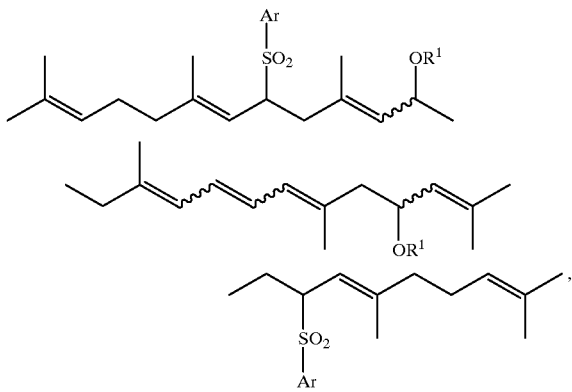

(4)

wherein Ar represents an aryl group which may be substituted, $R^1$ represents a lower alkyl group or a protective group of a hydroxyl group, and the wavy line depicted by "〜" indicates a single bond and stereochemistry relating to a double bond bound therewith is E or Z or a mixture thereof, which comprises reacting a phosphonlium salt of formula (3):

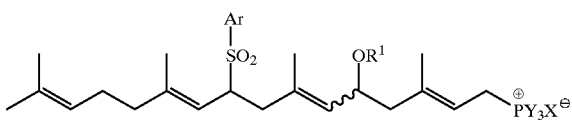

(3)

wherein Ar, $R^1$ and the wavy line respectively have the same meanings as defined above, X represents a halogen atom or $HSO_4$, and Y represents a lower alkyl group or an optionally substituted aryl group, with a sulfonaldehyde derivative of formula (2):

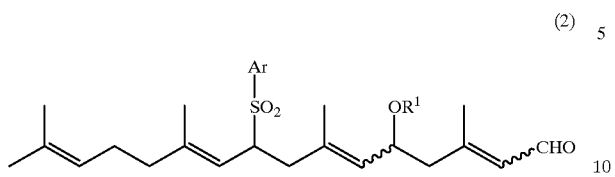
(2)

wherein Ar, R¹ and the wavy line have the same meanings respectively as defined above, in the presence of a base or an epoxide.

12. A process according to claim 11, wherein said phosphonium salt of formula (3) is a compound obtained by a process comprising reacting a sulfone alcohol derivative of formula (1):

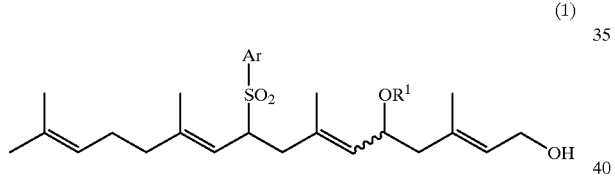
(1)

wherein Ar, R¹ and the wavy line respectively have the same meanings as defined with a salt of a tertiary phosphine compound and a protonic acid, or with a tertiary phosphine compound in the presence of a protonic acid, wherein said tertiary phosphine compound has the same meaning as defined.

13. A process according to claim 11, wherein said sulfonaldehyde derivative of formula (2) is a compound obtained by a process comprising oxidizing a sulfone alcohol derivative of formula (1):

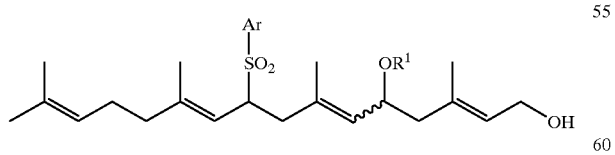
(1)

wherein Ar, R¹ and the wavy line respectively have the same meanings as defined for formula (2).

14. A process according to claim 13, wherein said phosphonium salt of formula (3) is a compound obtained by a process comprising reacting a sulfone alcohol derivative of formula (1):

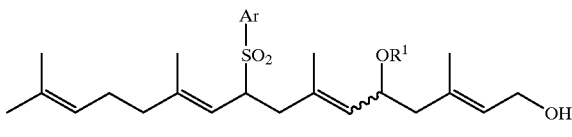
(1)

wherein Ar, R¹ and the wavy line respectively have the same meanings as defined for the phosphonium salt of formula (3) with a salt of a tertiary phosphine compound and a protonic acid, or with a tertiary phosphine compound in the presence of a protonic acid.

15. A sulfone derivative of formula (4) as defined in claim 11.

16. A process for producing lycopene of formula (5):

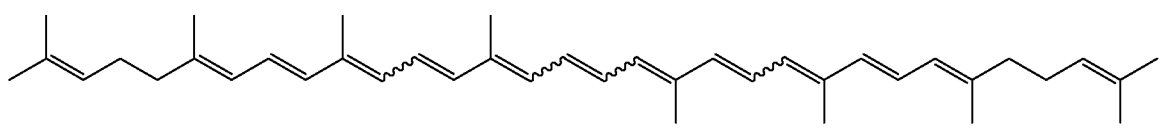
(5)

wherein wavy line depicted by "⌇" indicates a single bond and stereochemistry relating to a double bond bound therewith is E or Z or a mixture thereof, which comprises reacting a sulfone derivative of formula (4)

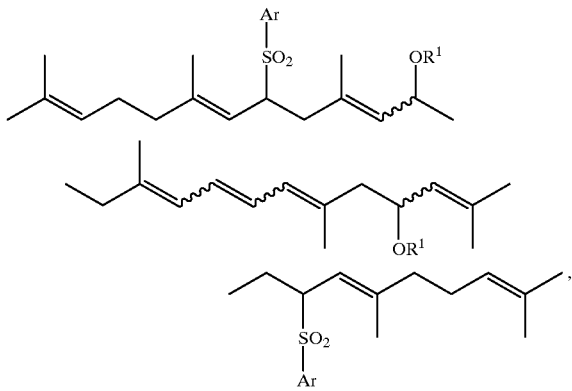
(4)

wherein Ar represents an aryl group which may be substituted,

R¹ represents a lower alkyl group or a protective group of a hydroxyl group, and the wavy line depicted by "⌇" indicates a single bond and stereochemistiy relating to a doubLe bond bound therewith is E or Z or a mixture thereof, with a basic compound.

17. A process according to claim 11, 12, 13 or 14, which further comprises reacting the sulfone derivative of formula (4) with a basic compound to produce lycopene of formula (5):

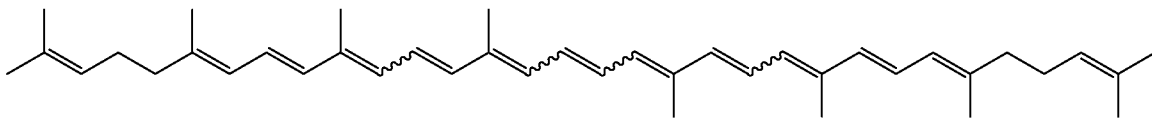

(5)

wherein the wavy line depicted by "〰" indicates a single bond and stereochemistry relating to a double bond bound therewith is E or Z or a mixture thereof.

18. A process according to claim 7, 9, 10, 11, 12 13 and 14, wherein the salt of a tertiary phosphine compound is triphenylphophine hydrochloride, triphenylphosphine hydrobromide or triphenylphoephine hydroiodide.

19. A process according to claim 7, 11, 12 13 or 14, wherein the protonic acid is hydrogen chloride, hydrogen bromide, hydrogen iodide or sulfuric acid.

20. A process for producing lycopene according to claim 16, wherein the basic compound is an alkali metal hydroxide or an alkali metal alkoxide.

* * * * *